(12) United States Patent
Guy et al.

(10) Patent No.: US 9,713,485 B2
(45) Date of Patent: Jul. 25, 2017

(54) PELVIC BONE PLATE

(71) Applicant: Stryker European Holdings I, LLC, Kalamazoo, MI (US)

(72) Inventors: Pierre Guy, Vancouver (CA); Henry Claude Sagi, Tampa, FL (US); Michael Archdeacon, Cincinnati, OH (US); Jakob Kemper, Lo Barnechea/Santiago (CL); Matthias Paulisch, Solothurn (CH); Andreas Petersik, Hamburg (DE)

(73) Assignees: Stryker GmbH (CH); Stryker European Holdings I, LLC, Kalamazoo, MI (US)

( * ) Notice: Subject to any disclaimer, the term of this patent is extended or adjusted under 35 U.S.C. 154(b) by 0 days.

(21) Appl. No.: 15/149,402

(22) Filed: May 9, 2016

(65) Prior Publication Data
US 2016/0249963 A1 Sep. 1, 2016

Related U.S. Application Data

(63) Continuation of application No. 14/172,298, filed on Feb. 4, 2014, now Pat. No. 9,358,053.
(Continued)

(51) Int. Cl.
*A61B 17/80* (2006.01)
*A61B 17/68* (2006.01)

(52) U.S. Cl.
CPC .......... *A61B 17/8066* (2013.01); *A61B 17/80* (2013.01); *A61B 17/8061* (2013.01); *A61B 2017/681* (2013.01)

(58) Field of Classification Search
CPC ...................... A61B 17/8066; A61B 17/8061
See application file for complete search history.

(56) References Cited

U.S. PATENT DOCUMENTS

| 2,580,821 A | 1/1952 | Nicola |
| 4,029,091 A | 6/1977 | von Bezold et al. |
| (Continued) | | |

FOREIGN PATENT DOCUMENTS

| DE | 3839859 A1 | 8/1989 |
| EP | 1897509 A1 | 3/2008 |
| (Continued) | | |

OTHER PUBLICATIONS

Acumed, Locking Scapula Plate System, 2008.
(Continued)

*Primary Examiner* — David Bates
(74) *Attorney, Agent, or Firm* — Lerner, David, Littenberg, Krumholz & Mentlik, LLP

(57) ABSTRACT

A bone plate has a first frame portion with a plurality of apertures. The apertures may have central axes angled with respect to a bone contacting surface adjacent thereto at an angle of other than 90°. The plate has a second plate portion comprising a plurality of apertures therethrough and has a first end connected to the first plate portion. The plate has a third plate portion having first and second ends respectively connected to a second end of the second plate portion and to the first plate portion at a point thereon closer to a center of the first plate portion than the first end of the second plate portion to the first plate portion. The first, second and third plate portions having an arcuate shape capable of conforming to an arcuate bone surface, the bone contacting surface forming a concave portion of the arcuate shape.

20 Claims, 8 Drawing Sheets

Related U.S. Application Data

(60) Provisional application No. 61/771,210, filed on Mar. 1, 2013.

(56) References Cited

U.S. PATENT DOCUMENTS

| | | | |
|---|---|---|---|
| 4,219,015 A * | 8/1980 | Steinemann | A61B 17/80 606/280 |
| 4,403,607 A | 9/1983 | Woo et al. | |
| 4,454,876 A | 6/1984 | Mears | |
| 4,800,874 A | 1/1989 | David et al. | |
| 5,006,120 A | 4/1991 | Carter | |
| 5,326,367 A | 7/1994 | Robioneck et al. | |
| 5,690,631 A | 11/1997 | Duncan et al. | |
| 5,746,742 A | 5/1998 | Runciman et al. | |
| 5,941,878 A | 8/1999 | Medoff | |
| 6,004,353 A | 12/1999 | Masini | |
| 6,306,173 B1 | 10/2001 | Masini | |
| 6,440,131 B1 | 8/2002 | Haidukewych | |
| 6,840,959 B2 | 1/2005 | Treacy et al. | |
| 2002/0042654 A1 | 4/2002 | Masini | |
| 2003/0105464 A1 | 6/2003 | Schreurs et al. | |
| 2004/0097936 A1 | 5/2004 | Ebid | |
| 2004/0186477 A1 | 9/2004 | Winquist et al. | |
| 2005/0165401 A1 | 7/2005 | Pack | |
| 2006/0241592 A1 * | 10/2006 | Myerson | A61B 17/8061 606/280 |
| 2007/0083204 A1 | 4/2007 | Sidebotham | |
| 2009/0275987 A1 | 11/2009 | Graham et al. | |
| 2011/0046681 A1 | 2/2011 | Prandi et al. | |
| 2012/0226279 A1 | 9/2012 | Lutz et al. | |

FOREIGN PATENT DOCUMENTS

| | | |
|---|---|---|
| EP | 2494934 A1 | 9/2012 |
| FR | 590290 A | 6/1925 |
| FR | 2906126 A1 | 3/2008 |
| JP | 2004-154480 A | 6/2004 |
| WO | 01/78616 A1 | 10/2001 |
| WO | 2010037985 A1 | 4/2010 |

OTHER PUBLICATIONS

European Search Report for Application No. 14156221.5 dated Jul. 7, 2014.
European Search Report, EP 1157015, dated Aug. 4, 2011.
Grade-5 (6Al-4V-3.7 165-R56400) Titanium. Material Property Database, accessed on Sep. 19, 2012. <http://www.makeitfrom.com/material-data/?for=Grade-5-6Al-4V-3.7 165-R56400-Titanium.
Stryker Trauma AG, SPS Matta Pelvic System, 2006.

* cited by examiner

PELVIC BONE PLATE

CROSS-REFERENCE TO RELATED APPLICATION

This application is a continuation of U.S. application Ser. No. 14/172,298 filed Feb. 4, 2014, which claims benefit of U.S. Provisional Patent Application No. 61/771,210 filed Mar. 1, 2013, the disclosures of which are hereby incorporated herein by reference.

BACKGROUND OF THE INVENTION

The invention relates to a pelvic and scapular bone plate implant and a surgical method for implanting such a pelvic or, alternatively, a scapular bone plate implant.

Surgical methods are known for reconstructing a patient's anatomy after a bone fracture. These procedures rely on the surgeon's use of metallic plates or meshes which are screwed to a fractured bone in order to reset comminuted areas of the fractured bone. These plates may carry the load of the comminuted area of the bone. Due to the rigidity of the plate, the fractured bone can heal in the proper position, because motion is minimized. These strong plates must usually be contoured to the surface shape of the bone. An example for a fixation plate is shown in U.S. Pat. No. 4,454,876 which discloses a pelvic fixation plate and method of implanting the same. Also see the Matta Pelvic System sold by Stryker® Corporation. However, with the plates from the state of the art, especially with plates for larger surfaces, it can be very challenging to bend the plate correctly with respect to the anatomical region. A pressure on an inside shape can be achieved by contouring the plate beyond the bending extent required for the plate to touch the bone surface in that area, but it is very difficult for a surgeon to adjust the slope and this can lead to a suboptimal fit along the outer edges.

The quadrilateral surface of the pelvis is often affected by high impact pelvic fractures, because the femoral head is driven from the acetabulum through the quadrilateral surface towards the inner pelvis. This results in a comminuted fracture of the quadrilateral surface. Especially since the center of this wall between inner pelvis and acetabulum is very thin and has to be buttressed in order to re-establish the acetabular surface. However, under consideration of the above difficulties encountered when forming the known plates, there is potential for improvement in plates for buttressing contoured large-area bones.

A deformable pelvic/scapular plate is shown in U.S. Patent Publication No. 2012/0226279, the disclosure of which is incorporated herein by reference.

BRIEF SUMMARY OF THE INVENTION

It is one aspect of the invention to provide a pelvic bone plate implant, a pelvic or scapular bone plate implant, a surgical method for implanting the pelvic bone plate implant and a surgical method for implanting the scapular bone plate implant, in order to improve the buttressing of a fractured bone.

A bone plate is provided which has a first plate portion having first and second ends and having a plurality of apertures. The first plate portion has a surface for contacting bone, at least one of the plurality of apertures has a central axis angled with respect to the bone contacting surface adjacent thereto at an angle of other than 90°. A second plate portion has a plurality of apertures therethrough with the second plate portion having a first end connected to the first plate portion. A third plate portion has first and second ends. The first end of the third plate portion is connected to a second end of the second plate portion and has a second end connected to the first plate portion at a point thereon closer to a center of the first plate portion than the connection between the first end of the second plate portion to the first plate portion. The bone contacting surface of the first, second and third plate portions has an arcuate shape capable of conforming to an arcuate bone surface. The bone contacting surface forming a concave portion of the arcuate shape.

The third plate portion preferably has a width less than a width of the first and second plate portions and the third plate portion is free of apertures. The second plate portion is connected to the first plate portion adjacent the first end thereof. The second end of the first bone plate portion defines a plate longitudinal axis and further comprises a fourth plate portion extending from the first plate portion second end in a direction perpendicular to a longitudinal axis of the first plate second end. All of the bone plate apertures are preferably non-threaded. At least one aperture has a part-spherical seating surface spaced from the bone contacting surface towards an outwardly facing bone plate surface. This aperture can receive a handle for gripping and inserting the plate.

The at least one aperture in the plate having a part-spherical seating surface is located on the first plate portion. The part-spherical seating surface preferably has an 8.5 mm radius. The first, second and third plate portions may define an opening having a generally triangular shape. The bone plate is preferably made of an implant grade stainless steel about 2.5 mm thick. The first and second bone plate portions may include a total of at least 12 apertures. The first plate portion may comprise at least eight apertures, the second plate portion comprises at least three apertures and the fourth plate portion comprises two apertures. The second and third plate portions may be connected to the first plate portion by first and second bridge portions respectively, the bridge portions being free of apertures. The apertures may have a central axis angled with respect to the bone contacting surface are angled at between 25 and 95 degrees thereto. The angled holes are preferably not threaded and accommodate 3.5 mm and 4.5 mm bone screws. One of the non-threaded aperture is capable of receiving an attachment handle for plate insertion. This aperture may be centrally boated on the first bone plate part. There may be 16 apertures in all the plate parts including an aperture dedicated for the attachment of a handle for plate insertion.

The bone plate implant may be formed from one piece of material wherein the boundary of the frame portion surrounds at least 80% of the circumference of the central opening. Preferably the outer frame portion is a closed frame. The second and third plate portions may be connected with the outer frame portion via material bridges. The outer frame portion may be provided with a plate segment projecting in a direction in parallel to an imaginary bending axis of the material interconnection. The frame portion can have a substantially triangular shape with a central open portion wherein the central open portion is also substantially triangular. A plurality of apertures are provided along the outer frame portion for fixing the bone plate implant.

A scapular bone plate implant is also provided which comprises a planar or curved outer frame portion having a frame surface which can be aligned to a bone-surface of a bone to which the scapula bone plate implant is to be implanted. Again a frame with a central opening is provided.

The outer frame portion at least partially surrounds the central open portion such that on the bone-surface, the central open portion is located within the outer dimensions of the outer frame portion. The scapular plate has similar features to the pelvic plate described above.

A surgical method for implanting the pelvis bone plate implant set forth above comprises pre-bending the outer frame portion according to the shape of the bone, pre-bending the bone contacting surfaces of the frame portions towards an area of the bone to be buttressed, implanting the pelvic bone plate implant by fixing it to the pelvis. The pre-bending of the outer frame portion involves contouring the outer frame portion to the shape of the pelvis area to which the bone plate implant is to be applied. The longest frame portion may have an extension (i.e., the fourth plate portion) which is bent over the pelvic bone edge surface. The surgical method for implanting the scapula bone plate implant includes pre-bending the outer frame portion according to the shape of the bone specifically pre-bending frame portions towards an area of the bone to be buttressed, implanting the scapula bone plate implant by fixing it to the scapula with bone screws. The method for fixing a fracture of a pelvic or scapular bone may comprise determining the size and location of the fractured bone and obtaining a bone plate of appropriate size having a frame portion having a surface which can conform to a surface of a bone to which the bone plate implant is to be implanted.

The definitions given in this summary are valid throughout the entire specification. A "material interconnection" is a connection in which the connected parts are fixed to each other by atomic or molecular forces. These are non-detachable connections which can only be separated by destruction of the connection. Preferably, the material interconnection is integrally formed. More preferably, the material interconnection is formed monolithically. Thus, a bone plate made from a single stamped metal plate would exhibit such properties.

According to a yet further aspect of the invention, the bone plate implant is formed monolithically from one piece of for example implant grade stainless steel. This way, the bone plate implant can be manufactured comparatively inexpensively and the material interconnection can be formed easily without encountering any jointing problems.

Preferably, the outer frame portion surrounds, in the bone-surface contacting area, at least 80% of the circumference around the central open portion. More preferably, the outer frame portion is a closed frame. The more the outer frame portion is closed, the more stabilizing and rigid it will be.

According to a yet further aspect of the invention, the pelvis bone plate implant further comprises a plurality of apertures provided along the outer frame portion for fixing the bone plate implant. These apertures function as holes for positioning and holding fastening means, e.g. bone screws or nails, in order to fasten the bone plate implant to the bone.

As used herein when referring to bones or other parts of the body, the term "proximal" means close to the heart and the term "distal" means more distant from the heart. The term "inferior" means toward the feet and the term "superior" means toward the head. The term "anterior" means toward the front part or the face and the term "posterior" means toward the back of the body. The term "medial" means toward the midline of the body and the term "lateral" means away from the midline of the body.

DETAILED DESCRIPTION

Figure 1:
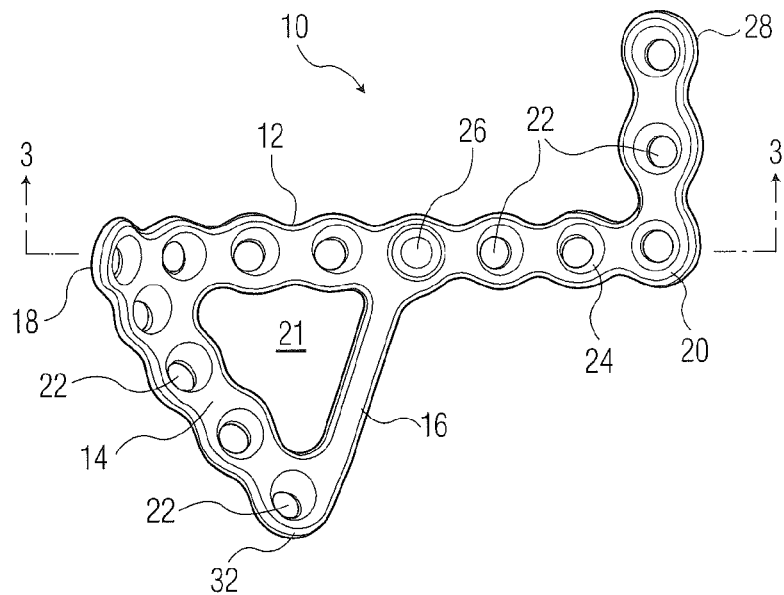
FIG. 1 is a plan view of the pelvic/scapular bone plate of the present invention.
Figure 2:
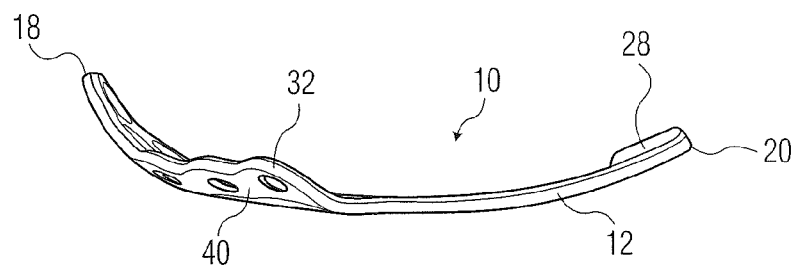
FIG. 2 is an elevation view of the bone plate of FIG. 1.
Figure 3:
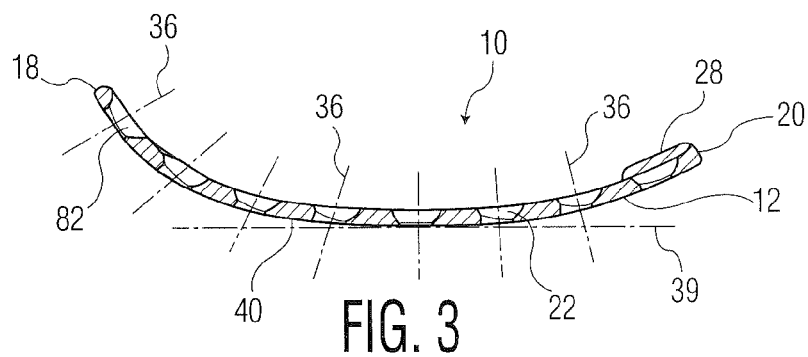
FIG. 3 is a cross-sectional view of the bone plate of FIG. 1 along lines 3-3.

Referring to FIGS. 1 to 3 there is shown a first embodiment of a pelvic or scapular bone plate generally designated as 10 which can consist of a first frame portion 12, a second frame portion 14 and a third frame portion 16. Frame portion 12 includes a first end 18 and a second end 20. Frame portions 12 and 14 include a series of apertures 22 which include part spherical seats 24 for receiving polyaxial bone screws. Plate 10 may include a central opening 26 along frame portion 12 which can be attached an insertion instrument (not shown) used during implanting the bone plate in the pelvis or scapula. First portion 12 includes a fourth plate portion in the form of an extension portion 28 at first end 20. Extension portion 28 extends generally perpendicular to the axis through the first portion 12. Third plate portion 16 is preferably narrower than first and second plate portions 12 and 14 and has no apertures 22. The first, second and third frame portions enclose a generally triangular opening 21.

Bone plate implant 10 may be flat or pre-bent and is a large area plate for covering major parts of the quadrilateral surface of the pelvis. In other words, the thickness of the bone plate 10 is compartively small when compared to a dimension in the direction of the bone contacting surface 40 which is supported by contact between the bone plate 10 and the bone. The bone plate thickness is preferably 2 to 5 mm which allows the surgeon to perform additional bending of the plate frame portions intraoperatively. This is especially true with the extension 28 which can be bent over the pelvis. The plate is preferably formed of titanium, or preferably titanium alloy Ti 6Al 4V, or formed of implant grade stainless steel preferably type 1.441. If titanium is used, the Young's modulus would be about 110,000 $N/mm^2$, and in the case of implant grade stainless steel, the Young's modulus would be about 210,000 $N/mm^2$. Titanium is preferred because it is easier to bend. The area covered by the first, second and third bone plate portions may be, at least in part, a triangle with the second and third frame portions forming two sides of the triangle. Typically the third frame portion side 16 will attach to second portion 14 at an apex 32 shown in FIG. 1. While the shape of plate 10 can be changed by hand, the surgeon may also use appropriate bending tools to form the plate.

Referring to FIG. 2, there is shown an elevation view of plate 10 of FIG. 1 showing it being curved in two dimensions to match the bone of the pelvis. Likewise, referring to FIG. 3, there is shown a cross-sectional view along lines 3-3 of FIG. 1 which is a longitudinal axis bisecting the holes 22 on first frame portion 12 again showing the curve of plate portion 12. It can be seen that the axes 36 of apertures 22 with respect to a tangent 39 through the bottom most part of FIG. 3 vary so that bone screws inserted therethrough do not inpinge on one another.

As can be seen in FIG. 3, the axis 36 of apertures 22 may vary from 60 to 110° with respect to the tangent 39 through the bone contacting surface 40 of plate 10.

Figure 4:
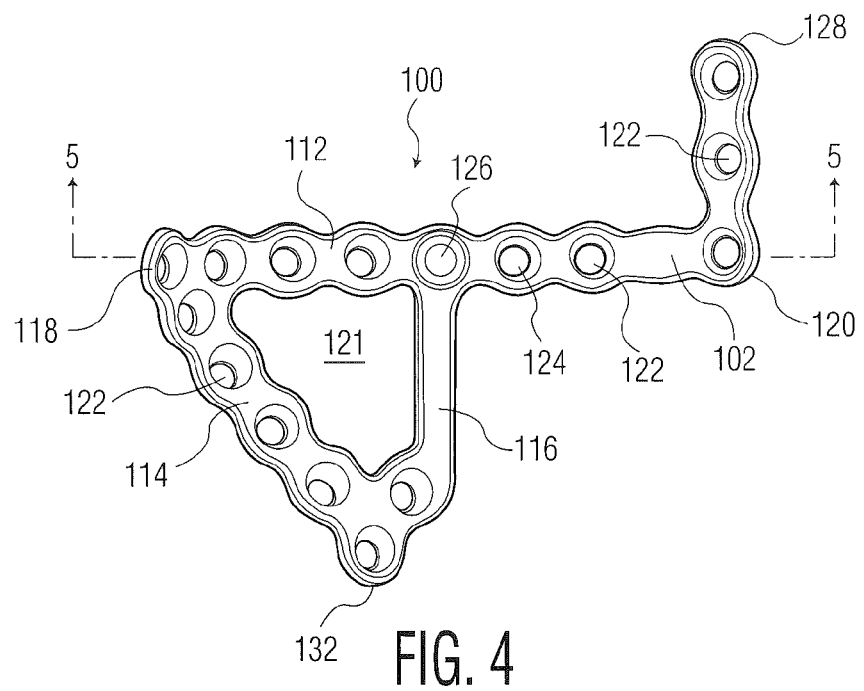
FIG. 4 shows a top view of a second embodiment of the present invention including an enlarged frame.
Figure 5:
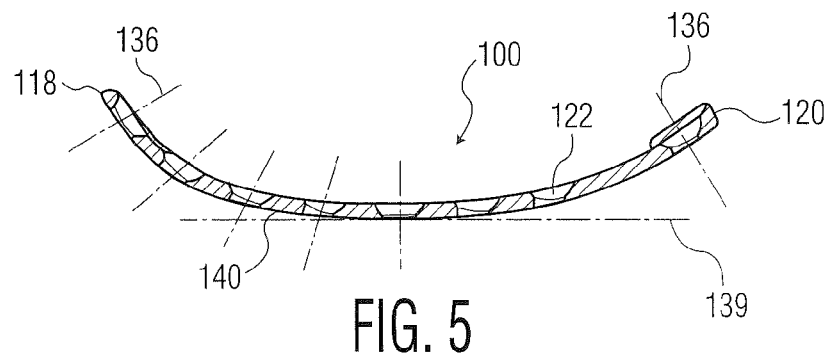
FIG. 5 is a cross-sectional view of the bone plate of FIG. 4 along lines 5-5.

Referring to FIGS. 4-5, there is shown a second embodiment of a pelvic or scapular bone plate generally designated as 100. This plate is similar to that shown in FIG. 1 except it has an extended portion 102 forming part of first frame portion 112. Like the bone plate of FIG. 1, the bone plate of FIG. 4 includes a second frame portion 114 and a third frame portion 116 surrounding an open area 121. Again open area 125 is generally triangular in shape. Similar apertures 122 which include part-spherical seats 124 are located along the first and second frame portions. First frame portion 112 extends from a first end 118 to a second end 120 with an extension 128 again extending from the second end 120 of first frame portion 112. Second frame portion 114 and third frame portion 116 meet at apex 132. It should be noted that bone plate 100 has additional apertures 122 because of its larger size. An aperture 122 is located at apex 132 to ensure the tip of the plate 100 is fixed flat to the bone.

Figure 4A:
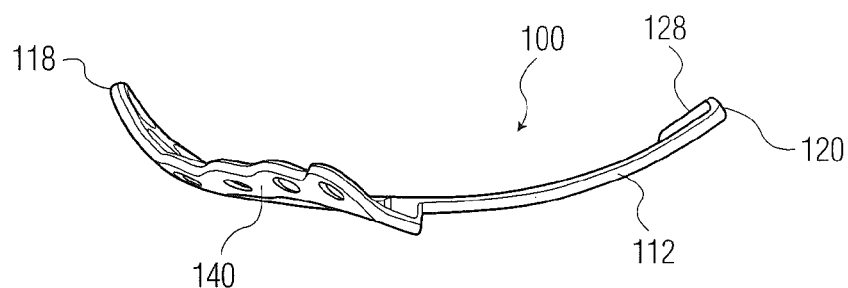
FIG. 4A shows the bone plate of FIG. 4 in elevation.

Referring to FIG. 4A there is again shown an elevation view of the plate of FIG. 4 including a bone contacting surface 140 and extension portion 128. Referring to FIG. 5 there is shown a cross-sectional view of the plate of FIG. 4 along lines 5-5 of FIG. 4 which again is an axis bisecting the holes 122 extending along first frame portion 112. Again the screw axis of holes 122 are angled with respect to one another so that when a plurality of bone screws are inserted through a number of apertures 122 respectively there is no impingement between the threaded shafts of the screw.

Figure 6:
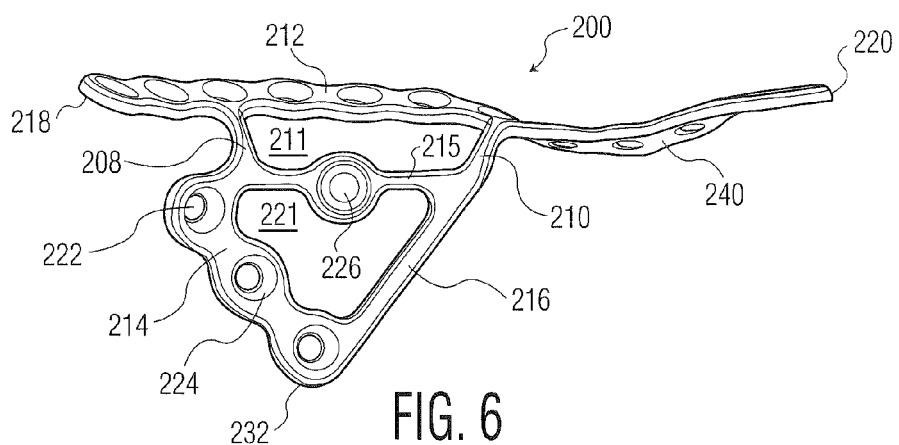
FIG. 6 is a top view of a third embodiment of a bone plate of the present invention.
Figure 7:
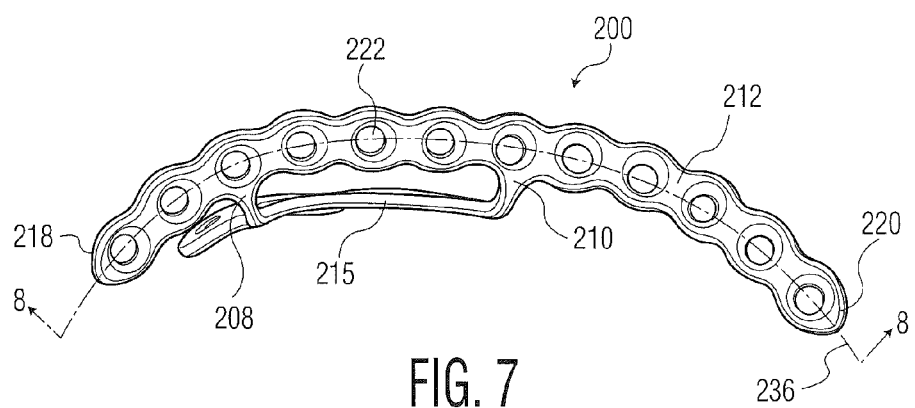
FIG. 7 is a side view of the bone plate of FIG. 6.
Figure 8:
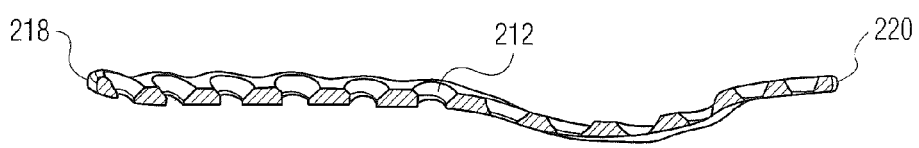
FIG. 8 is a cross-sectional view along the axis 8-8 of FIG. 7.

Referring to FIGS. 6-8, there is shown a third embodiment of a plate of the present invention generally denoted as 200. Plate 200 includes a first frame portion 212 having a first end 218 and a second end 220. However, in this design, the generally triangular opening 221 is spaced from first plate portion 212 by bridge portion 208 and 210 which thereby form an open space 211. Space 211 is surrounded by frame portion 212, bridge portions 208 and 210 as well as a fourth plate portion 215. Fourth plate portion 215 is generally parallel to first plate portion 212 and forms a frame portion of generally triangular opening 221. As with the other plates, an aperture 226 is provided for connecting to an insertion tool to be used by the surgeon to insert the bone plate 200 into the pelvis or scapula. However, instead of being part of the first plate portion 212 it is part of the fourth plate portion 215. Thus, the generally triangular open space 221 formed by the second, third and fourth connection portions 214, 215 and 216 respectively has the tool aperture 226. Second plate portion 214 and third plate portion 216 meet at an apex 232. Apertures 222 in the first and second plate portions 212 and 214 with the part spherical seating surfaces 224 are provided entirely along the first and second portions 212, 214 of bone plate 200. Bridge portions 208 and 210 are made relatively narrow so that the plate portion formed by frame members 214, 215 and 216 can be easily bent with respect to first frame portion 212.

Referring to FIG. 7 there is shown plate 200 of FIG. 6 when viewed from the top showing the preferably twelve (12) apertures 222 which extend along plate portion 212 between ends 218 and 220. Referring to FIG. 8 there is a cross-sectional view of the bone plate of FIGS. 6 and 7 along axis 8-8 of FIG. 7 which generally bisects the apertures 220 therealong. As with bone plates 10 and 100 axis 236 through each of the 12 apertures 222 vary to ensure that the bone screws inserted therethrough do not interfere with one another. As with the other plate designs, the plate 200 can be bent intraoperatively so that bone contacting surface 240 thereof conforms to the shape of the pelvic bone which has the fracture.

Figure 9:
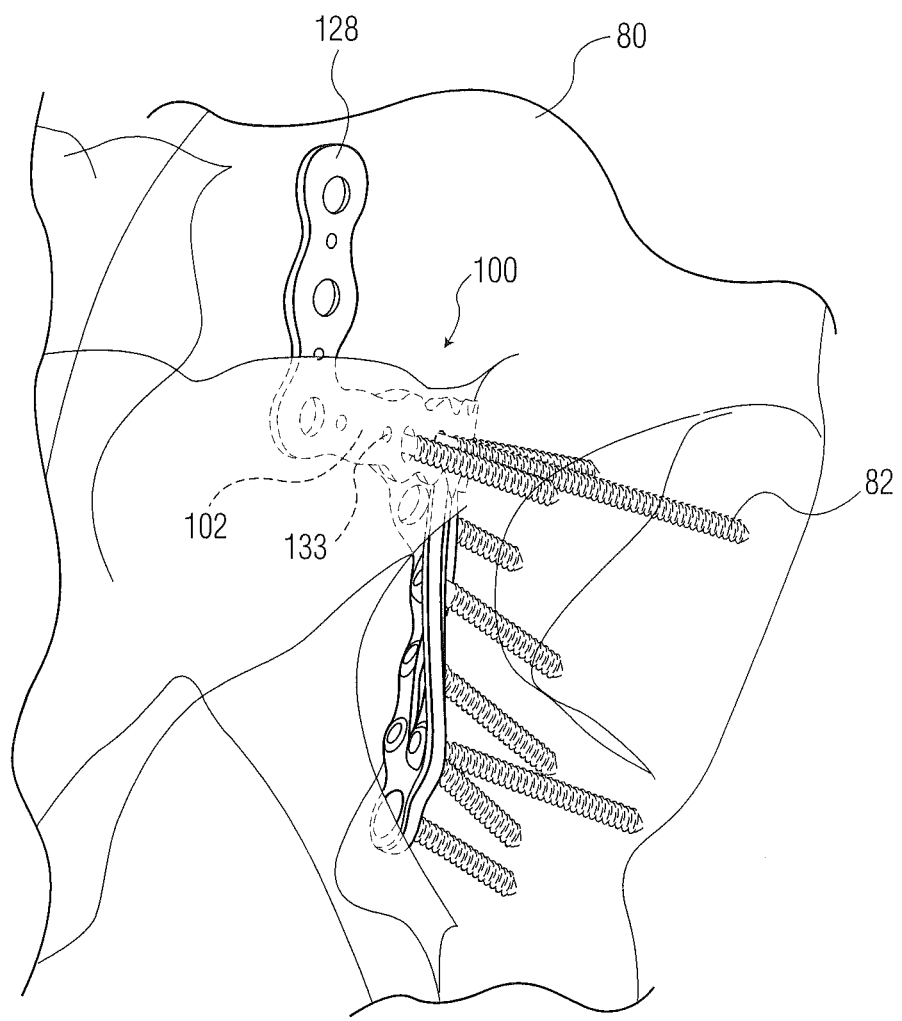
FIG. 9 shows the plate of the present invention used for infrapectineal plating of an acetabular fracture from a first side of the pelvis.
Figure 10:
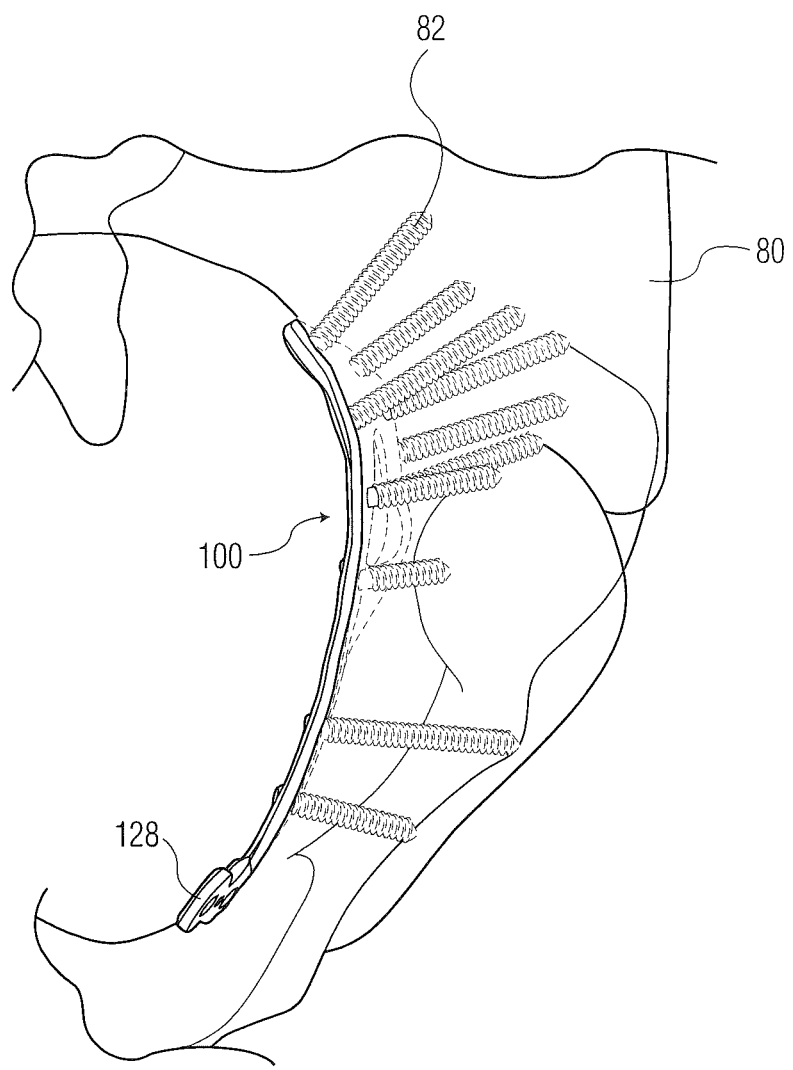
FIG. 10 is a top view of the plate of FIG. 9 mounted on the pelvis.
Figure 11:
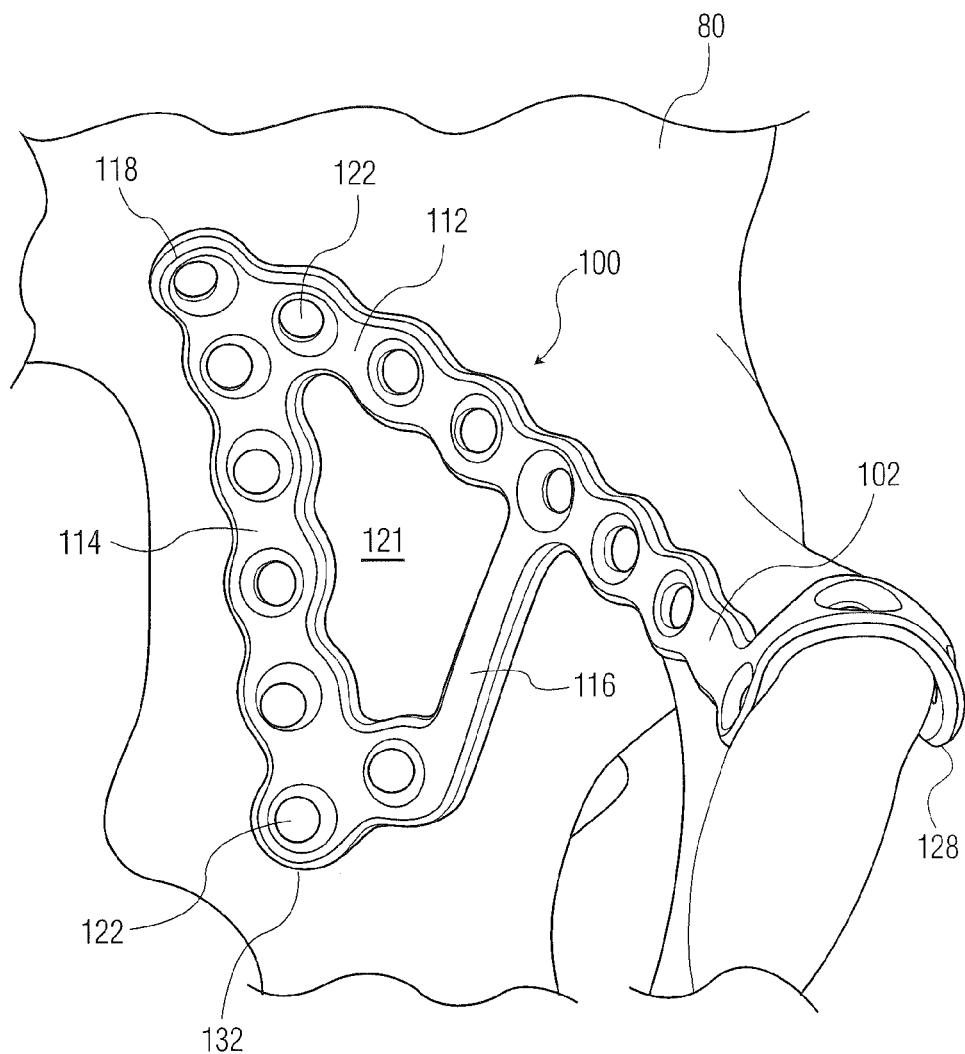
FIG. 11 shows the plates of FIGS. 9 and 10 with an extension introperatively bent over the pelvis.

Referring to FIG. 9 there is shown bone plate 100 mounted in a pelvis 80 a plurality of bone screws 82 extending into the bone of the pelvis 80. Referring to FIG. 10 there is shown the bone plate of FIG. 9 when viewed from above including the plurality of bone screws 82 extending into the pelvis 80. Referring to FIG. 11 there is shown the bone plate 100 mounted on pelvis 80 with the extended portion 128 deformed over the pelvic bone. As shown in FIG. 11 the bone plate 100 and extension 120 is deformed prior to inserting bone screws 82.

Figure 12:
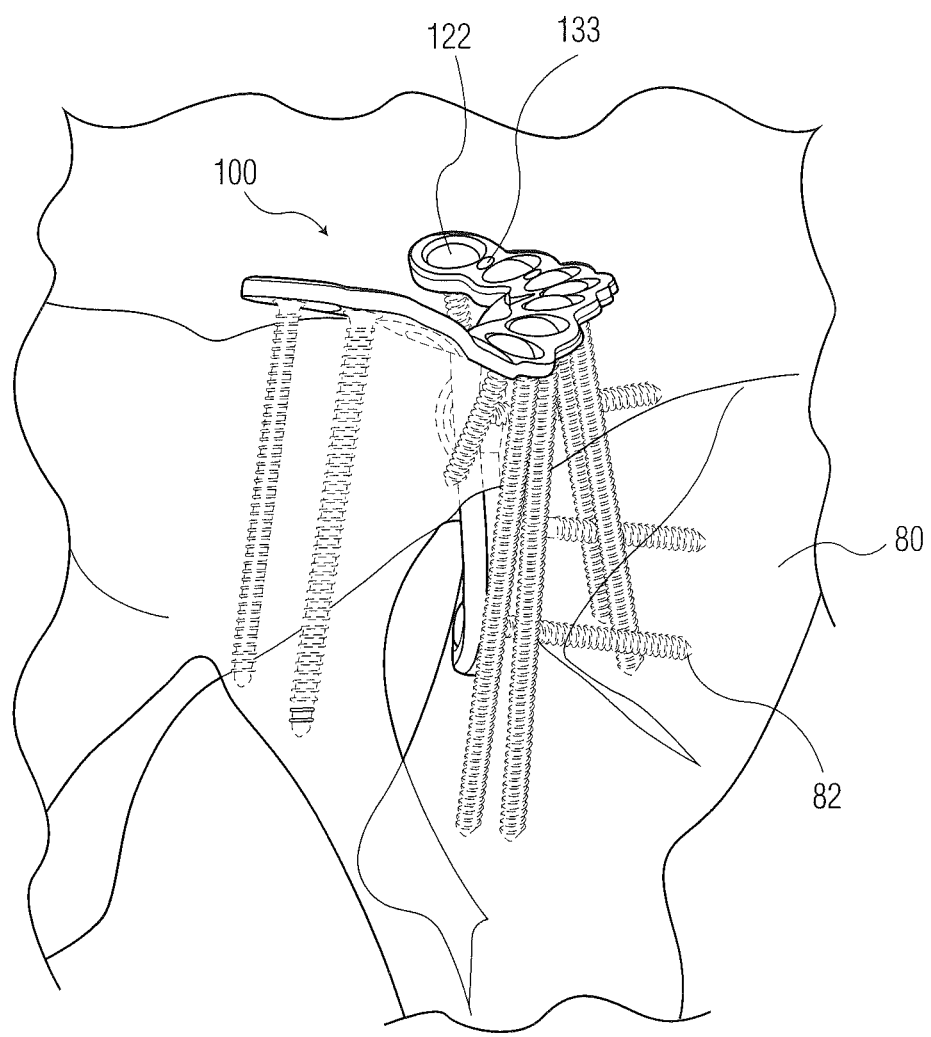
FIG. 12 shows one of the plates of FIGS. 1-8 used as a suprapectineal plate to plate an acetabular fracture.
Figure 13:
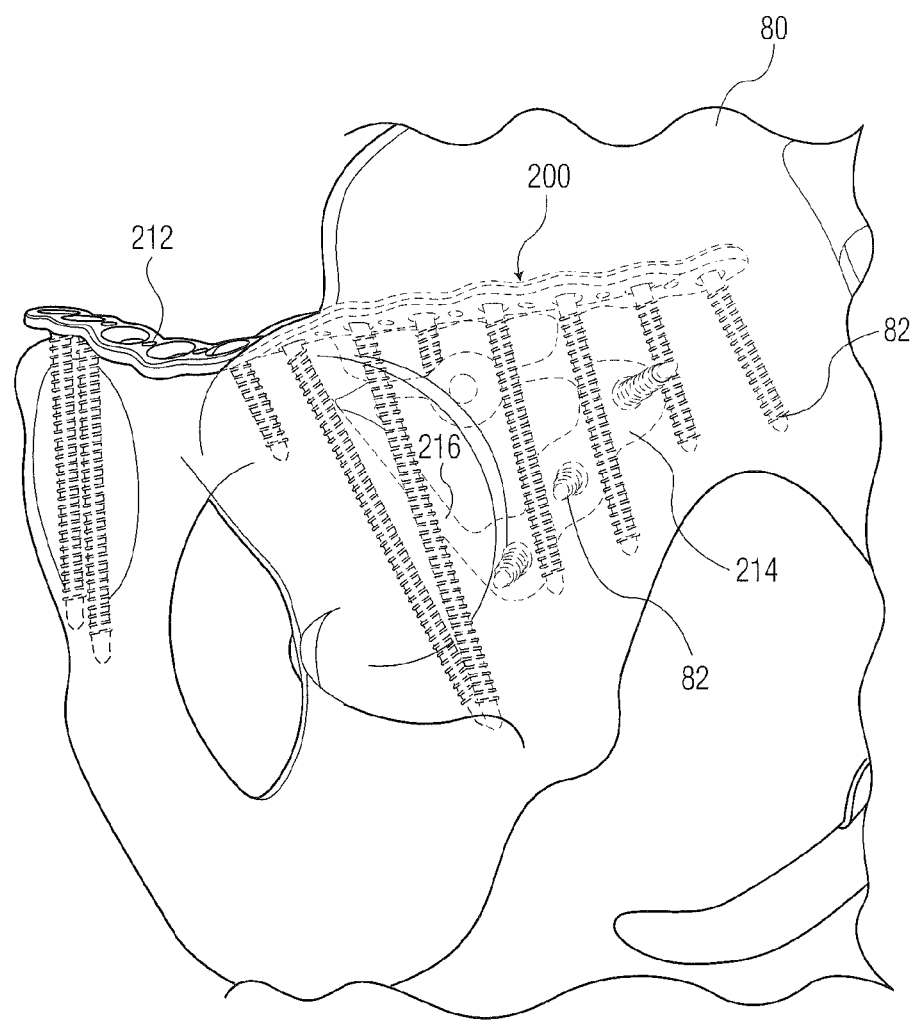
FIG. 13 shows the plate of FIG. 12 from a front view.

Referring to FIG. 12 there is shown the bone plate of FIG. 11 after a plurality of bone screws are inserted through apertures 122 as can be seen in FIG. 12 several small diameter apertures 133 may be provided for Kirschner wires which are temporarily inserted to hold the bone plate in position prior to inserting bone screws 82. Referring to FIG. 13 there is shown bone plate 200 mounted on pelvis 80 with a plurality of bone screws 82 with the second and third portions 214 and 216 shown in phantom as being located on the opposite side of the pelvic bone.

While the invention has been illustrated and described in detail in the drawings and foregoing description, such illustration and description are to be considered illustrative or exemplary and not restrictive and it is not intended to limit the invention to the disclosed embodiments. The mere fact that certain measures are recited in mutually different dependent claims does not indicate that a combination of these measures cannot be used advantageously. Any reference signs in the claims should not be construed as limiting the scope of the invention.

The invention claimed is:

1. A bone plate comprising:
   a first plate portion comprising a bone contacting surface and a plurality of bone screw receiving apertures extending therethrough, a center of each aperture located along an arcuate longitudinally extending axis;
   first and second bridge portions extending from the first plate portion to a second plate portion, the second plate portion having an aperture therethrough, the second plate portion extending generally parallel to the first plate portion, the first and second bridge portions, the first plate portion and the second plate portion forming four sides of an open space located therebetween;
   a third plate portion extending from a first end of said second plate portion at a non-ninety degree angle, the third plate portion having a plurality of apertures therethrough; and
   a fourth plate portion extending from a second end of the second plate portion at a non-ninety degree angle and having an end coupled to an end of the third plate portion, the second plate portion, the third plate portion and the fourth plate portion defining a generally triangular opening therebetween with the second plate portion forming a base of the triangular opening, and the third and fourth plate portions joined at an apex of the triangular opening, the apex and first plate portion being on opposite sides of the second plate portion, the generally triangular opening defined by the second, third and fourth plate portions capable of being located below the bone contacting surface of the first plate portion by deformation of the first and second bridge portions.

2. The bone plate as claimed in claim 1 wherein the first opening is generally rectangular.

3. The bone plate as claimed in claim 1 wherein the first plate portion contains twelve apertures.

4. The bone plate as claimed in claim 1 wherein the fourth plate portion is free of apertures.

5. The bone plate as claimed in claim 1 wherein the third plate portion has three bone screw receiving apertures.

6. The bone plate as claimed in claim 1 wherein the aperture in the second portion is located midway between the third and fourth plate portions.

7. The bone plate as claimed in claim 1 wherein the first plate portion is generally planar with a central axis of each bone screw receiving aperture extending transverse to the plane of the first plate portion.

8. The bone plate as claimed in claim 7 wherein the second, third and fourth plate portions lie in a plane and are capable of being bent about the bridge portions to a position lying in a plane transverse to a plane of the first plate portion.

9. The bone plate as claimed in claim 8 wherein after bending the plane of the second, third and fourth plate portions extends perpendicularly to the plane of the first plate portion.

10. The bone plate as claimed in claim 8 wherein the second, third and fourth plate portions extend in a direction towards the bone contacting surface of the first plate portion.

11. A bone plate comprising:
a first longitudinally extending plate portion having an upper surface and a lower bone contacting surface and a plurality of bone screw receiving apertures extending from the upper surfaces to the bone contacting surface;
first and second bridge portions connected to the first plate portion and extending from the first plate portion to a second plate portion spaced from the first plate portion, the first plate portion, the second plate portion and the first and second bridge portions defining an open space therebetween; and
a third and fourth plate portion, first ends of the third and fourth plate portions connected to the second plate portion, second ends of the third and fourth plate portion connected to one another and spaced from the second plate portion, the second, third and fourth plate portions defining a generally triangular opening therebetween, the connection of the second ends of the third and fourth plate portions forming an apex of the generally triangular opening, the second, third and fourth plate portions capable of being oriented in a direction generally perpendicular to the bone contacting surface of the first plate portion by deformation of the first and second bridge portions.

12. The bone plate as claimed in claim 11 wherein the bone screw receiving apertures in the first plate portion are circular with centers of each circular aperture lying on an arcuate longitudinal axis.

13. The bone plate as claimed in claim 11 wherein the second ends of the third and fourth plate portions meet at a point intermediate a length of the second plate portion.

14. The bone plate as claimed in claim 11 wherein the first opening is generally rectangular.

15. The bone plate as claimed in claim 11 wherein the first frame portion contains twelve bone screw receiving apertures.

16. The bone plate as claimed in claim 11 wherein the fourth plate portion is free of apertures.

17. The bone plate as claimed in claim 11 wherein the second plate portion has one bone screw receiving aperture.

18. The bone plate as claimed in claim 11 wherein the bone screw receiving aperture in the second plate portion is located midway between the third and fourth plate portions.

19. The bone plate as claimed in claim 11 wherein the first plate portion is generally planar with a central axis of each aperture extending transverse to the plane of the first plate portion.

20. The bone plate as claimed in claim 11 wherein the third plate portion has a upper surface and a bone contacting surface with a plurality of bone screw receiving apertures extending from the upper surface to the bone contacting surface.

* * * * *

UNITED STATES PATENT AND TRADEMARK OFFICE
CERTIFICATE OF CORRECTION

PATENT NO. : 9,713,485 B2
APPLICATION NO. : 15/149402
DATED : July 25, 2017
INVENTOR(S) : Pierre Guy et al.

Page 1 of 1

It is certified that error appears in the above-identified patent and that said Letters Patent is hereby corrected as shown below:

In the Claims

Column 7, Lines 9-10, "first opening" should read --open space--.
Column 8, Lines 22-23, "first opening" should read --open space--.
Column 8, Line 32, "claim 11" should read --claim 17--.

Signed and Sealed this
Twenty-ninth Day of May, 2018

Andrei Iancu
*Director of the United States Patent and Trademark Office*